United States Patent [19]

Birkenstock et al.

[11] 4,265,834

[45] May 5, 1981

[54] PROCESS FOR THE CATALYTIC HYDROGENATION OF NITROBENZENE

[75] Inventors: Udo Birkenstock, Ratingen; Burkhard Lachmann, Meerbusch; Josef Metten, Krefeld; Herbert Schmidt, Leverkusen, all of Fed. Rep. of Germany

[73] Assignee: Bayer Aktiengesellschaft, Leverkusen, Fed. Rep. of Germany

[21] Appl. No.: 66,977

[22] Filed: Aug. 16, 1979

[30] Foreign Application Priority Data

Nov. 11, 1978 [DE] Fed. Rep. of Germany ....... 2849002

[51] Int. Cl.$^3$ ............................................. C07C 85/11
[52] U.S. Cl. ................................. 564/421; 252/469; 252/470; 252/472; 252/474
[58] Field of Search ............... 260/580; 252/469, 470, 252/472, 474

[56] References Cited

U.S. PATENT DOCUMENTS

| | | | |
|---|---|---|---|
| 2,823,235 | 2/1958 | Graham et al. | 260/580 |
| 3,265,636 | 8/1966 | Spiegler | 260/580 X |
| 3,472,897 | 10/1969 | Pryor et al. | 260/580 |
| 3,666,813 | 5/1972 | Hindin et al. | 260/580 |
| 3,781,227 | 12/1973 | Sokolsky et al. | 260/580 X |
| 3,804,779 | 4/1974 | Kent et al. | 260/580 X |
| 4,137,254 | 1/1979 | Larkin | 260/580 X |

*Primary Examiner*—John Doll
*Attorney, Agent, or Firm*—Sprung, Felfe, Horn, Lynch & Kramer

[57] ABSTRACT

A process for the hydrogenation of nitrobenzene to aniline is described wherein the nitrobenzene is contacted with hydrogen in the presence of a multi-component supported catalyst containing 1 to 20 grams of noble metal per liter of support and 1 to 20 grams per liter of support of one or more transition metal of the Groups IVa, Va, or VIa of the Periodic Table. The catalyst can contain 1 to 20 grams per liter of support of a further transition group element or of a member of the main group. The catalyst is one which has been prepared by a process involving pretreatment of the support with a base prior to impregnation with the catalytically active substances, followed by drying to a residual moisture content of less than 10 percent of the maximum absorbency of the support.

17 Claims, No Drawings

PROCESS FOR THE CATALYTIC HYDROGENATION OF NITROBENZENE

CROSS-REFERENCE TO RELATED APPLICATIONS

This application is related to U.S. Ser. No. 066,986, filed Aug. 16, 1979, entitled HYDROGEN CATALYST, corresponding to German application Ser. No. P 28 49 026.8 and U.S. Ser. No. 066,976, filed Aug. 16, 1979, entitled SUPPORTED CATALYSTS, THEIR PREPARATION AND USE, corresponding to German application Ser. No. P 28 48 978.3.

BACKGROUND OF THE INVENTION

1. Field of the Invention

The present invention relates to a process for the catalytic hydrogenation of nitrobenzene to aniline in the gas phase using a palladium-containing supported catalyst.

2. Discussion of Prior Art

Palladium-containing supported catalysts for carry-out catalytic hydrogenation reactions, inter alia also of nitro-aromatic compounds, are generally known. The supports used industrially as the starting base material for the corresponding supported catalysts have, however, considerable disadvantages. Thus, because of the nature of their surface, the support materials are not inert and therefore as a rule cause undesired by-products to be formed. Furthermore, the application of the palladium to these supports in general results in a uniform distribution of the Pd over the entire grain of the support. This results in unnecessarily high catalyst costs, since, as is known, the active substances deposited inside the grain of the support either take no part in the reaction to be catalyzed or participate in this reaction to only a minor extent. For example, aluminum spinels, especially alkali metal or alkaline earth metal spinels, are employed as support materials for palladium catalysts for the reduction of nitroaromatic compounds. When such alkali metal aluminum spinels or alkaline earth metal aluminum spinels are prepared, varying residual amounts of water-soluble alkali metal or alkaline earth metal remain dispersed in the grain of the support, due to the process. Due to this inhomogeneity of the spinel, inhomogeneous deposition of the active substances in the individual grains of the support necessarily results. As a consequence of this, undesired differences in activity, selectivity and life arise when these aluminum spinel catalysts are employed industrially German (BRD) Offenlegungsschrift 2,135,155.

Since the catalytic hydrogenation of nitrobenzene to aniline is a large-scale industrial process an aniline is required in large amounts as an important intermediate product in the preparation of pharmaceuticals and dyestuffs and duct in the preparation of pharmaceuticals and dyestuffs and of monomers for polymerization, there continues to be a growing interest in improving this process by eliminating the above mentioned disadvantages.

SUMMARY OF THE INVENTION

It has now been found that the hydrogenation of nitrobenzene to aniline, in the presence of supported catalysts containing a noble metal, in the gas phase at elevated temperature can be carried out with the greatest possible selectivity, very little by-product formation and long catalyst lives, such as have not been expected hitherto, with constant catalyst activity, if the hydrogenation is carried out in the presence of a multi-component supported catalyst which contains 1 to 20 g of a noble metal per liter of support material and 1 to 20 g of one or more transition metals of groups IVa, Va or VIa of the periodic table of the elements (Mendelejew) per liter of support material, the said metals being in the form of the elements or in the form of a compound optionally the catalyst can additionally obtain 1 to 20 g of a further transition group element or main group element, in the form of the elements or in the form of a compound, per liter of support material, the inert support having a BET surface area of less than 20 m$^2$/g and, prior to application of the catalytically active components, which is effected in a manner which is in itself known, having been pre-treated with a base and then dried to a residual moisture content of less than 10% of the maximum absorbency of the support.

Preferably, three-component catalysts on which 1 to 10 g of noble metal per liter of support material and 5 to 15 g of one or more transition metals, preferably vanadium, niobium, tantalum, chromium, molybdenum, tungsten or titanium, per liter of support material, the said metals being in the form of the elements or in the form of any desired compound, preferably in the form of an oxygen-containing compound, and also, optionally, 1 to 10 g of a further transition group element or main group element, preferably one of the elements lead, zinc or bismuth, in the form of the element or in the form of any desired compound, per liter of support material, have been deposited are used in the process according to the invention, the inert support material being, for example, $\alpha$-Al$_2$O$_3$ with a BET surface area of less than 20 m$^2$/g and preferably less than 10 m$^2$/g, which has been pretreated by the action of a base and subsequent drying to a residual moisture content of preferably less than 5%, particularly preferentially less than 2% and very particularly preferentially less than 1% of the absorbency of the support before it is impregnated with the solution of the noble metal salt, preferably a solution of a palladium salt, and with one or optionally more additional components, for example vanadium salts, lead salts or bismuth salts.

The term noble metals is understood as meaning metals of groups VIIIa, Ib and IIb of the periodic table according to Mendeleev. Examples which may be mentioned individually are Fe, Ru, Os, Co, Rh, Ir, Ni, Pd, Pt, Cu, Ag, Au, Zn, Cd and Hg. Particularly preferentially, palladium is employed as the noble metal. A metal of groups IVb and Vb, for example lead or bismuth, may be mentioned as a main group element.

The process according to the invention can be operated in all of the types of reactors suitable for gas phase hydrogenation, such as, for example, tube reactors, fluidized bed reactors or cage reactors. Preferably, the process according to the invention is carried out in tube reactors with a fixed catalyst. It can be carried out either at normal pressure or under excess pressure or reduced pressure. In general, the reaction is operated at approximately normal pressure under the temperature conditions known for catalytic hydrogenation of nitroaromatic compounds. The heat of reaction is removed by means of a suitable heat carrier liquid, the temperature of which is kept in a range of about 150° to 350° C. and preferably to 200° to 300° C.

Before flowing through the catalyst bed, the nitrobenzene is vaporized in a vaporizer in a stream of hydrogen with at least 3 mols of hydrogen and preferably 1 to 10 mols of hydrogen per mol of nitrobenzene, in a temperature range of about 100° to 300° C. and preferably 150° to 250° C. The excess hydrogen is usually cycled with the removal of a small partial stream from the system. After flowing through the reactor, the hydrogenation product is condensed.

Materials used as the support materials which are pretreated with bases by the process according to the invention are very diverse systems from which the inert support material with a BET surface area of less than 20 m$^2$/g and preferably less than 10 m$^2$/g has been built up. These materials are essentially metal oxides, silicates, spinels, carbides, carbonates and the like and mixtures thereof. Inert support materials are particularly preferred, such as, for example, aluminum oxides, silicon dioxides, silicon dioxide/aluminum oxide mixtures, amorphous silica, kieselguhr, barium, strontium or calcium carbonates, mixtures thereof, optionally with the addition of silicon dioxides or aluminum oxides, titanium oxides, zirconium oxides, magnesium oxides, magnesium silicates, zirconium silicates, magnesium aluminum spinel, silicon carbides, tungsten carbides, mixtures of silicon carbides with silicon dioxides or any desired mixtures thereof. The inert supports can be used in very diverse forms, such as, for example, in the form of spheres, granules, extrudates, tablets, saddle-shaped pieces, tube sections, fragments, honeycomb ceramics and the like.

The special features of the preparation of the supported catalysts used in the process according to the invention are described briefly below:

The treatment of the inert support e.g. $\alpha$-Al$_2$O$_3$, which is particularly preferred as the support material, with a base is usually carried out at temperatures of 10° to 60° C. Preferably, 0.5 to 20 gram equivalents of base per gram equivalent of noble metal, e.g. palladium are employed. Preferred bases are alkali metal hydroxides, alkaline earth metal hydroxides, alkali metal carbonates, alkali metal bicarbonates and alkali metal acetates. They are usually employed in the form of solutions in water or in non-aqueous solvents, such as aliphatic alcohols with 1 to 4 C atoms or aliphatic ketones, such as, for example, acetone, or in mixtures thereof. The particularly preferred bases are sodium hydroxide and potassium hydroxide.

The drying of the support material to the indicated residual moisture content, which follows the treatment with a base, is essential. In general it is carried out at 50° to 200° C., preferably at 100° to 150° C., and under pressures of ≦1 bar.

The support which has been pretreated with the base is then impregnated, in accordance with its absorbency, to saturation in a manner which is in itself known with a palladium salt solution, the Pd content of which is determined by the amount of base previously applied. Optionally, the Pd salt applied is reduced to the metal before, in the next preparation step, one or more of the transition metals of groups IVa, Va or VIa of the periodic table according to Mendeleev, for example V, Cr, Mo, W, Nb, Ta and Ti, is applied in the form of any desired metal salt solution, for example in the form of the metal oxalate solution. It can also be advantageous to carry out the impregnation with the noble metal salt solution at the same time as the impregnation with the transition metal salt, for example to apply Pd together with Cr in the form of their chlorides. After drying and subsequent decomposition of the metal salt at about 200° to 500° C., and preferably 250° to 400° C., the support material is optionally impregnated, in a further preparation step, with a solution of a salt of a transition or main group element of groups IIb, IVb and Vb, preferably with a solution of a lead and/or bismuth salt.

It is essential for the preparation of the supported catalysts used in the process according to the invention that, as a result of the nature of the pretreatment of the support with a base and the subsequent drying, the deposition of active substance, especially the deposition of noble metal, takes place within a narrow, outer annular zone just below the surface of the support. When they are employed industrially in the hydrogenation of nitrobenzene, the catalysts prepared in accordance with this principle and used in the process according to the invention produce fewer byproducts than conventional hydrogenation catalysts, because of the small surface area of the inert support material. Furthermore, the active substances enriched in the support are substantially protected against poisoning and losses due to abrasion. As a result of this, a very long catalyst life with constant activity is achieved.

The following may be mentioned as examples of catalysts which are used in the process according to the invention for the catalytic hydrogenation of nitrobenzene to aniline in the gas phase:

TABLE 1

| Catalyst | Pd (g/l) | V (g/l) | Mo (g/l) | Cr (g/l) | Pb (g/l) | Bi (g/l) | Zn (g/l) |
|---|---|---|---|---|---|---|---|
| I | 9 | 9 | — | — | 3 | — | — |
| II | 9 | 6 | — | — | 3 | — | — |
| III | 6 | 9 | — | — | 3 | — | — |
| IV | 4.5 | 6 | — | — | 3 | — | — |
| V | 9 | 9 | — | — | — | — | — |
| VI | 9 | 12 | — | — | 3 | — | — |
| VII | 9 | 9 | — | — | — | 3 | — |
| VIII | 9 | — | 6 | — | 3 | — | — |
| IX | 9 | — | — | 7.2 | — | — | — |
| X | 9 | 12 | — | — | — | — | — |
| XI | 9 | 9 | — | — | — | — | 3 |

The examples which follow serve to further illustrate the process according to the invention.

EXAMPLE 1

Preparation of the catalyst

One liter of an $\alpha$-aluminum oxide support in the form of spheres with a diameter of 3 to 6 millimeters, a BET surface area of 9.8 m$^2$/g, an absorbency of 45.1 ml of water per 100 g of support and a bulk density of 812 g/l was impregnated with 366 ml of an aqueous solution containing 10.8 g, corresponding to 0.27 gram equivalent, of NaOH. The solution was completely absorbed by the support within a few minutes. The moist support was poured into a vertical glass tube with a capacity of about 2 l and dried in a stream of warm air at 120° C., the amount of air being 25 Nm$^3$ of air per hour. The drying time to constant weight was about 30 minutes. After cooling to room temperature, the residual moisture content was about 0.9% of the absorbency of the support.

The dry support pretreated in this way was impregnated, in accordance with its absorbency, with 366 ml of an aqueous solution of sodium tetrachloropalladate-II, which contained 9 g of palladium, corresponding to 0.169 gram equivalent, and left to stand for 15 minutes. In order to reduce the palladium compound deposited on the support to metallic palladium, the support was covered, in a glass beaker, with a layer of 400 ml of a 10% strength aqueous solution of hydrazine hydrate and left to stand for 2 hours. The catalyst was then washed in a running stream of distilled water until no further ions of the compounds used in the preparation of the catalyst were detectable in the wash water. This was the case after 10 hours.

The subsequent drying was carried out in a stream of warm air, as described above for drying of the support. The catalyst prepared in this way contained 9 g of palladium per liter of support.

The Pd-containing catalyst was then impregnated with 366 ml of an aqueous solution containing 9 g of vanadium in the form of vanadyl oxalate. Drying of the Pd catalyst impregnated with vanadyl oxalate was carried out analogously to the drying of the support in a stream of warm air at 120° C. The subsequent decomposition of the vanadyl oxalate was carried out at 300° C. over the course of 6 hours.

After this treatment, the catalyst was impregnated with 366 ml of an aqueous solution containing 3 g of lead in the form of lead acetate. The catalysts impregnated with lead acetate was filled, in the moist state, into a tube reactor and dried during the heat-up period of the heat carrier.

Activation of the catalyst was carried out in a stream of hydrogen at the temperature of the heat carrier, which was 280° C. The finished catalyst contained, calculated as the metals, 9 g of palladium, 9 g of vanadium and 3 g of lead per liter of support. It corresponds to catalyst I in Table 1.

EXAMPLE 2

A tube reactor (55 tubes; tube diameter 25 mm; tube length 3,500 mm) was filled with 85 liters of catalyst I (see the table) prepared according to Example 1. A gaseous mixture of nitrobenzene/hydrogen with a molar ratio of 1:6 was fed from bottom to top through the reactor which had been preheated to 280° C. with the heat carrier liquid "Marlotherm S". The charge was 0.47 kg of nitrobenzene per hour per liter of catalyst. After 1,450 hours, the reaction zone had migrated from the bottom to the top and regeneration was carried out. In the subsequent operating periods, the individual operating times were between 1,020 hours and 1,550 hours. A total life of 7,850 hours was achieved with the catalyst packing. The amount of aniline produced during this time was 236 tonnes. The catalyst consumption calculated from this is 0.36 liter of catalyst per tonne of aniline. The yield of aniline, based on the theoretical conversion of nitrobenzene, was 99.86% by weight.

EXAMPLE 3

A single tube hydrogenation reactor (tube diameter 32 mm; tube length 1,300 mm) was filled with 1 liter of catalyst II of Table 1. The catalyst was prepared analogously to Example 1 but 6 g of vanadium in the form of vanadyl oxalate were applied. The reactor temperature was kept at 260° to 270° C. by means of a boiling diphenyl/diphenyloxide mixture as the heat carrier. The nitrobenzene previously vaporized in a stream of hydrogen at 160° to 180° C., flowed, in the form of a gaseous nitrobenzene/hydrogen mixture (molar ratio of 1:6 ) through the reactor from bottom to top. The charge was maintained at 0.5 kg of nitrobenzene/hour×1 of catalyst. After leaving the reactor, the gaseous reaction product was condensed. The operating times of the individual operating periods were between 900 to 1,600 hours. The total life of the catalyst was 8,000 hours. 3,030 kg of aniline were produced in this time. This corresponds to a catalyst consumption of 0.33 l of catalyst/tonne of aniline. The aniline yield averaged over the total catalyst life was 99.85% of theory.

EXAMPLE 4

The catalytic gas phase hydrogenation of nitrobenzene to aniline was carried out in a single tube hydrogenation reactor analogously to Example 3 with catalyst III of Table 1. This catalyst was prepared analogously to Example 1. However, deviating from the instructions given in that example, impregnation was carried out with 366 ml of an aqueous solution containing 7.2 of NaOH (corresponding to 0.18 gram equivalent). The impregnation with palladium was carried out using 366 ml of an aqueous solution of sodium tetrachloropalladate-V, which contained 6 g of palladium, corresponding to 0.112 gram equivalent.

The operating times in the individual operating periods of achieved when carrying out the hydrogenation of nitrobenzene with this catalyst were between 1,100 hours and 1,360 hours.

| Results: | |
| --- | --- |
| Total catalyst life: | 6,140 hours |
| Catalyst consumption: | 0.43 1/tonne of aniline |
| Yield of aniline: | 99.81% by weight of theory |

EXAMPLE 5

The hydrogenation was carried out analogously to Example 3 using catalyst IV of Table 1. The catalyst was prepared analogously to Example 1, but impregnation was carried out with 5.4 g, corresponding to 0.135 gram equivalent, of NaOH. The impregnation with palladium was carried out using 4.5 g, corresponding to 0.084 gram equivalent, of palladium, and 6 g of vanadium in the form of vanadyl oxalate were employed for the deposition of vanadium. When nitrobenzene was hydrogenated using this catalyst, the operating times for the individual operating periods were between 1,000 hours and 1,430 hours.

| Results: | |
| --- | --- |
| Total catalyst life: | 7,650 hours |
| Catalyst consumption: | 0.35 1/tonne of aniline |
| Yield of aniline: | 99.87% by weight of theory |

EXAMPLE 6

Catalyst X of Table 1 was employed analogously to Example 3 for the hydrogenation of nitrobenzene. The catalyst was prepared analogously to Example 1, but 12 g of vanadium in the form of 366 ml of an aqueous solution of vanadyl oxalate were applied and the subsequent impregnation with lead was omitted.

| Results: | |
| --- | --- |
| Total catalyst life: | 6,450 hours |
| Catalyst consumption: | 0.41 hours/tonne of aniline |
| Yield of aniline: | 99.82% by weight of theory |

EXAMPLE 7

Catalyst XI of Table 1 was employed analogously to Example 3 for the hydrogenation of nitrobenzene. The catalyst was prepared analogously to Example 1, but the impregnation with lead was omitted and, instead of this, 3 g of zinc in the form of 366 ml of an aqueous solution of zinc acetate was applied.

Results:

| | |
|---|---|
| Total catalyst life: | 7,120 hours |
| Catalyst consumption: | 0.37 l/tonne of aniline |
| Yield of aniline: | 99.84% by weight of theory |

What is claimed is:

1. In a gas phase process for the catalytic hydrogenation of nitrobenzene to aniline wherein nitrobenzene is contacted with hydrogen in the presence of a catalyst, the improvement wherein said catalyst is a multi-component supported catalyst having a BET surface area of less than 20 square meters per gram and comprises 1 to 20 grams of a noble metal per liter of support and 1 to 20 grams of one or more transition metals of Groups IVa, Va, or VIa of the Periodic Table of the Elements per liter of support, said catalyst having been prepared by pretreating the support, prior to impregnation thereof with said noble method or said transition metal, with a base, thereafter drying the so-pretreated material to a residual moisture content of less than 10 percent of the maximum absorbency of the support and thereafter impregnating the support with 1 to 20 grams of said noble metal per liter of support and 1 to 20 grams of said transition metal per liter of support.

2. A process according to claim 1 wherein said catalyst additionally contains 1 to 20 grams per liter of support of a further transition group element or element of the main group.

3. A process according to claim 2 wherein the element of said further transition group element or main group element is an element of Group IIb, IVb, or Vb of the Period Table of the Elements.

4. A process according to claim 1 wherein said noble metal is present on said support in elemental form or in the form of a compound.

5. A process according to claim 4 wherein said transition metal of the Group IVa, Va, or VIa of the Periodic Table of the Elements is present on said support in the form of an element or in the form of a compound.

6. A process according to claim 2 wherein said further transition metal or transition metal of the main group is present on said support in elemental form or in the form of a compound.

7. A process according to claim 1 wherein said support material is α-alumina with a BET surface area of less than 10 square meters per gram.

8. A process according to claim 1 wherein the catalyst is prepared by drying the support material which has been pretreated with a base to a residual moisture content of less than 1 percent of the absorbency of the support before impregnating the same with said noble metal and said metal of the Group IVa, Va, or VIa.

9. A process according to claim 1 wherein the hydrogenation is carried out in the presence of a supported catalyst containing 1 to 10 grams palladium, 5 to 15 grams of one of the metals vanadium, niobium, tantalum, chromium, molybdenum, tungsten or titanium per liter of support.

10. A process according to claim 9 wherein said catalyst additionally contains 1 to 10 grams of a metal of the group of lead, zinc and bismuth.

11. A process according to claim 1 wherein the hydrogenation is carried out in the presence of a supported catalyst containing per liter of support 1 to 10 grams of palladium, 5 to 15 grams of vanadium and 1 to 10 grams of lead.

12. A process according to claim 1 wherein the base employed for the pretreatment is sodium hydroxide or potassium hydroxide.

13. A process according to claim 1 wherein said catalyst comprises 1 to 20 grams of palladium, 1 to 20 grams of molybdenum and 1 to 10 grams of lead, per liter of support.

14. A process according to claim 1 wherein said catalyst comprises 1 to 20 grams of palladium and 20 grams grams of chromium.

15. A process according to claim 1 wherein said catalyst comprises 1 to 20 grams of palladium, 1 to 20 grams of vanadium, and 1 to 10 grams of zinc, per liter of support.

16. A process according to claim 1 wherein the hydrogenation is carried out at 150° to 350° C.

17. A process according to claim 1 wherein the hydrogenation is carried out at 200°–300° C.

* * * * *